(12) United States Patent
Ghansham (10) Patent No.: US 11,266,446 B2
(45) Date of Patent: Mar. 8, 2022

(54) CLIP TYPE CRANIAL FLAP CLOSING AND ANCHORING DEVICE

(71) Applicant: Das Agarwal Ghansham, Shahjahanpur (IN)

(72) Inventor: Das Agarwal Ghansham, Shahjahanpur (IN)

( * ) Notice: Subject to any disclaimer, the term of this patent is extended or adjusted under 35 U.S.C. 154(b) by 0 days.

(21) Appl. No.: 15/532,709

(22) PCT Filed: Sep. 2, 2016

(86) PCT No.: PCT/IN2016/000224
§ 371 (c)(1),
(2) Date: Jun. 2, 2017

(87) PCT Pub. No.: WO2017/037736
PCT Pub. Date: Mar. 9, 2017

(65) Prior Publication Data
US 2017/0354440 A1 Dec. 14, 2017

(30) Foreign Application Priority Data
Sep. 4, 2015 (IN) .......................... 2780/DEL/2015

(51) Int. Cl.
*A61B 17/80* (2006.01)
*A61B 17/68* (2006.01)
*A61F 2/28* (2006.01)

(52) U.S. Cl.
CPC ........ *A61B 17/688* (2013.01); *A61B 17/8061* (2013.01); *A61F 2/2875* (2013.01)

(58) Field of Classification Search
CPC ... A61F 2/2875; A61B 17/80; A61B 17/8033; A61B 17/8061; A61B 17/8085; A61B 17/688
See application file for complete search history.

(56) References Cited

U.S. PATENT DOCUMENTS

| | | | | |
|---|---|---|---|---|
| 5,201,737 A | * | 4/1993 | Leibinger | A61B 17/688 606/280 |
| 5,961,519 A | * | 10/1999 | Bruce | A61B 17/8085 606/280 |
| 6,923,812 B1 | * | 8/2005 | Wellisz | A61B 17/685 606/151 |
| 8,425,515 B2 | * | 4/2013 | Gamache | A61B 17/7071 606/246 |
| 8,940,019 B2 | | 1/2015 | Gordon et al. | |
| 2002/0022844 A1 | * | 2/2002 | Vom Berg | A61B 17/688 606/71 |
| 2003/0100900 A1 | * | 5/2003 | Wellisz | A61B 17/688 606/75 |
| 2003/0100902 A1 | | 5/2003 | Wellisz et al. | |

(Continued)

FOREIGN PATENT DOCUMENTS

WO 2009086397 A2 7/2009
WO 2014097310 A1 6/2014

*Primary Examiner* — Si Ming Ku
(74) *Attorney, Agent, or Firm* — The Webb Law Firm (57) ABSTRACT

Provided herein is a clip type cranial flap closing and anchoring device having a single structure including first part in contact with top surface of the flap and second part in contact with bottom surface of said flap maintaining a gap therebetween to accommodate the flap, wherein the first part is fixedly secured to third part for fastening the device to the skull.

11 Claims, 6 Drawing Sheets

(56) References Cited

U.S. PATENT DOCUMENTS

| | | | |
|---|---|---|---|
| 2006/0287654 A1* | 12/2006 | Posnick | A61B 17/688 606/279 |
| 2011/0224734 A1* | 9/2011 | Schelling | A61B 17/7079 606/286 |
| 2015/0012047 A1 | 1/2015 | Agarwal | |
| 2015/0173815 A1* | 6/2015 | Breault | A61B 17/8061 606/286 |

* cited by examiner

CLIP TYPE CRANIAL FLAP CLOSING AND ANCHORING DEVICE

CROSS-REFERENCE TO RELATED APPLICATIONS

This application is the United States national phase of International Application No. PCT/IN2016/000224 filed Sep. 2, 2016, and claims priority to Indian Patent Application No. 2780/DEL/2015 filed Sep. 4, 2015, the disclosures of which are hereby incorporated in their entirety by reference.

FIELD OF INVENTION

This invention is related to a clip type cranial flap closing & anchoring device. This is particularly implemented to close and anchor bony cranial flap during neurosurgery of head (cranium) at cut lines.

BACKGROUND/PRIOR ART

Surgical operations inside the head/on the brain are performed after creating an opening in the skull (the bony cage around the brain or cranium). The standard method of opening is to make four/three burr holes (holes made with the help of burrs because burrs are slow cutters) followed by cutting in between the holes by means of giggly saw or modern craniotome (powered tools). The hard shell flap/bony flap/cranial flap thus created is either kept attached on one side with the pericranium or kept away from patient covered in a moist mop or in saline.

After finishing of operation on brain this flap needs to be reapplied by attaching with the skull. There are different ways to attach it.

Oldest method comprises drilling of a plurality of small holes in skull and the flap followed by passage of stainless steel wire there through.

Thereafter, the wire is twisted and cut to size followed by bending inside.

One of the newer methods is to employ two absorbable plastic buttons, one under the skull and one above the skull, wherein both buttons are tied with absorbable thread. This keeps the flap in position.

Another method involves two metal/titanium discs. One disc which goes under the skull has a serrated central wire, serrations of which are directed downwards. The second disc is threaded on the serrated wire. The second disc has a central hole with locking fins, wherein said second disc can be moved downwards only. Special instruments are needed to pull the wire through the second disc. Excess wire is cut off and second disc is locked on the skull.

However, the above discussed prior arts are associated with many disadvantages mentioned hereinbelow:

The first button design has poor stability and grip, which involves chances of flap slipping down. Further, the buttons are quite thick, which can be felt under skin and sometimes may look ugly if applied on exposed surface of head (forehead etc).

Further these buttons are expensive, application of which is time consuming.

Second design provides satisfactory anchorage. But it requires special & expensive instruments. Sometimes due to some complication or other reasons reoperation is required. The reoperation is cumbersome and also requires special tools. It is also time consuming affair and very expensive.

The aforesaid designs provide only limited stability to cranial flap. Slight push/pressure can push in the flap and damage brain.

In view of the above, there is a requirement to devise a cranial flap closing and anchoring device, which can address the shortcomings of the known arts and serve the purpose very efficiently.

OBJECTS OF INVENTION

An object of this invention is to propose a clip type cranial flap closing & anchoring device to be used at cut lines of cranium during neuro surgery of head.

Another object of this invention is to propose a clip type cranial flap closing & anchoring device, which is very fast to operate.

Still another object of this invention is to propose a clip type cranial flap closing & anchoring device, which is cost effective.

Still another object of this invention is to propose a clip type cranial flap closing & anchoring device, which does not need any special instrumentation for application.

Still another object of this invention is to propose a clip type cranial flap closing 86 anchoring device which prevents damage to brain.

Still another object of this invention is to propose a clip type cranial flap closing 86 anchoring device wherein reopening of craniotomy flap is fast and without need for special instrumentation.

Still another object of this invention is to propose a clip type cranial flap closing 86 anchoring device which is reusable.

Still another object of this invention is to propose a device which allows outward movement of cranial flap in case of brain edema.

SUMMARY OF THE INVENTION

According to this invention, there is provided a clip type cranial flap closing and anchoring device comprising a single structure including first part in contact with top surface of the flap and second part in contact with bottom surface of said flap maintaining a gap therebetween to accommodate the flap, wherein the first part is fixedly secured to third part for fastening the device to the skull.

BRIEF DESCRIPTION OF THE ACCOMPANYING DRAWINGS

Further objects and advantages of this invention will be more apparent from the ensuring description when read in conjunction with the accompanying drawings of exemplary embodiments of invention and wherein.

DETAIL DESCRIPTION OF THE INVENTION WITH REFERENCE TO THE ACCOMPANYING DRAWINGS

The present invention pertains to a clip type cranial flap closing & anchoring device, which can be called as cranial flap fixation device.

The device constitutes a single structure made of medical grade material. For the same, reference may be made to FIG. 1-4, wherein the device includes two parts (A, B) maintaining a gap therebetween.

Said first part (A) comprises a part having substantially U section. This part includes two arms (1, 2) which are running substantially parallel to each other and joined at one end by means of a connecting member (3). The connecting member (3) is fixedly secured to a third part. Said third part comprises an annular structure (4) having a tapered hole at the center so as to accommodate a screw for locking with the skull.

The two arms of the part having U-section are somewhat curved. The curved shape of the arms confirm to the profile of top surface of skull so as to remain intact with the top surface of cranium of head during surgery.

The second part (B) takes configuration of a substantially L-section as illustrated in the figure, which is provided in connection to the connecting member.

The gap between two parts (A, B) is equivalent to the thickness of cranium so as to develop firm grip while holding the cranium in the course of surgery.

There is a pin (P) having conical shape for example, which is projected from the surface of arm (5) of the second part (B), in which the pin is projected towards said part (A). The pin is sharp upward and backward directed arrow shaped. The pin is placed in proximity to end of the arm (5) of said part (B). Pointed part of the pin bites into the bone and helps in reducing chances of slippage of the device from the cranial flap.

Figure 8:
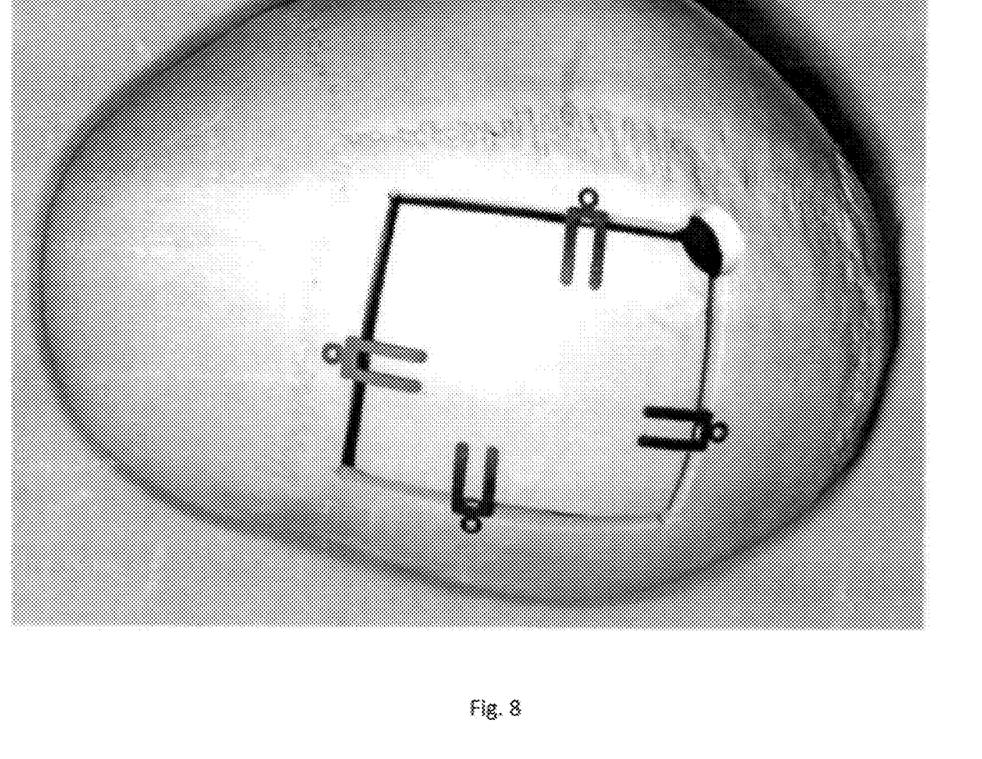
FIG. 8 shows: Placement of cranial flap on the skull opening.

At the end of the operation, said flap is placed on the skull opening as in FIG. 8.

In case required, surgeon can secure the device on to the skull by inserting screw in the hole of third part.

In this way, the device locks the cranial flap. Thus, neither inward nor outward movement of said flap is possible.

In case of reoperation/reopening of cranial flap the screws are unscrewed. The flap can be lifted by unlocking to be reopened. The same devices can be reused to close 85 lock the cranial flap.

In some cases where cerebral edema is expected, the cranial flap may not be locked. In other words in the devices, the screws are not applied. Inward movement of flap is prevented but outward movement is allowed. In case brain swells/of cerebral edema, the cranial flap allows outward movement and allows the brain to swell. On subsiding of edema the flap may come back to its original position.

The clip is made of medical grade biocompatible metal such as titanium without restricting scope of the invention to the same. Thus, other materials readily apparent to a person skilled in the art are understood to be within purview of invention.

Figure 1:
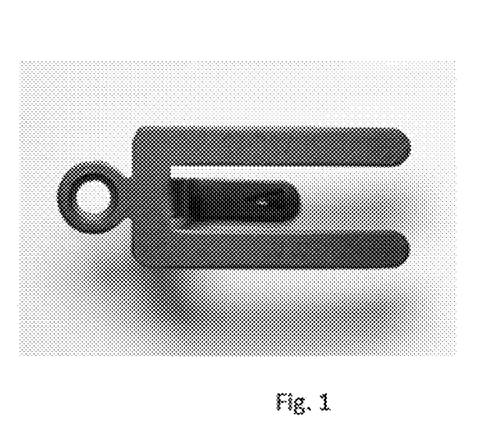
FIG. 1 shows: Top view of the clip type cranial flap closing and anchoring device of present invention.
Figure 2:
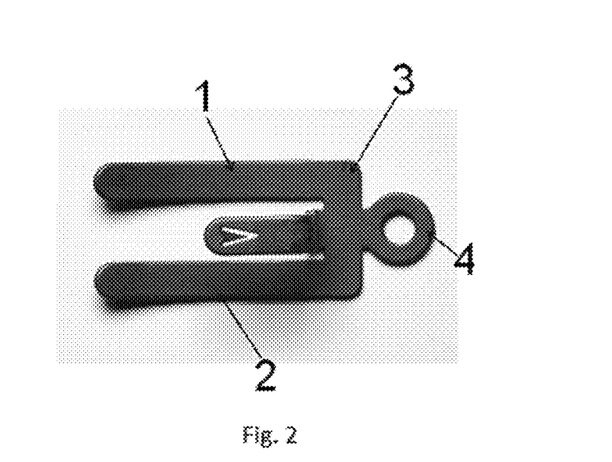
FIG. 2 shows: Bottom view of device according to present invention.
Figure 3:
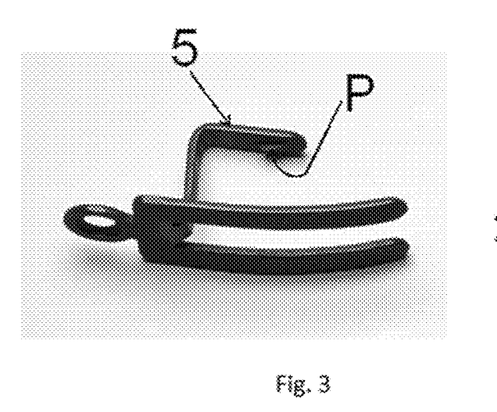
FIG. 3 shows: One side view of device in accordance with invention.
Figure 4:
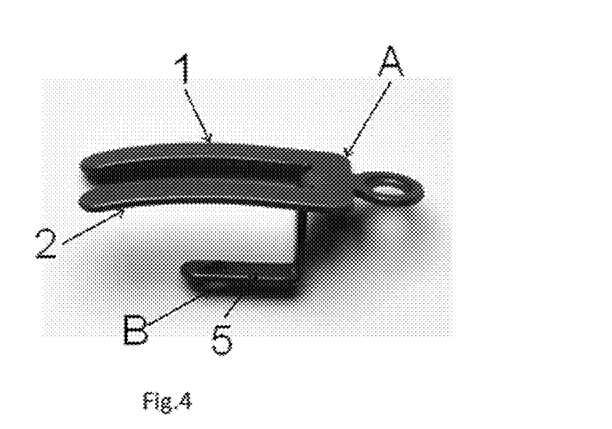
FIG. 4 shows: Another side view of device of present invention.
Figure 5:
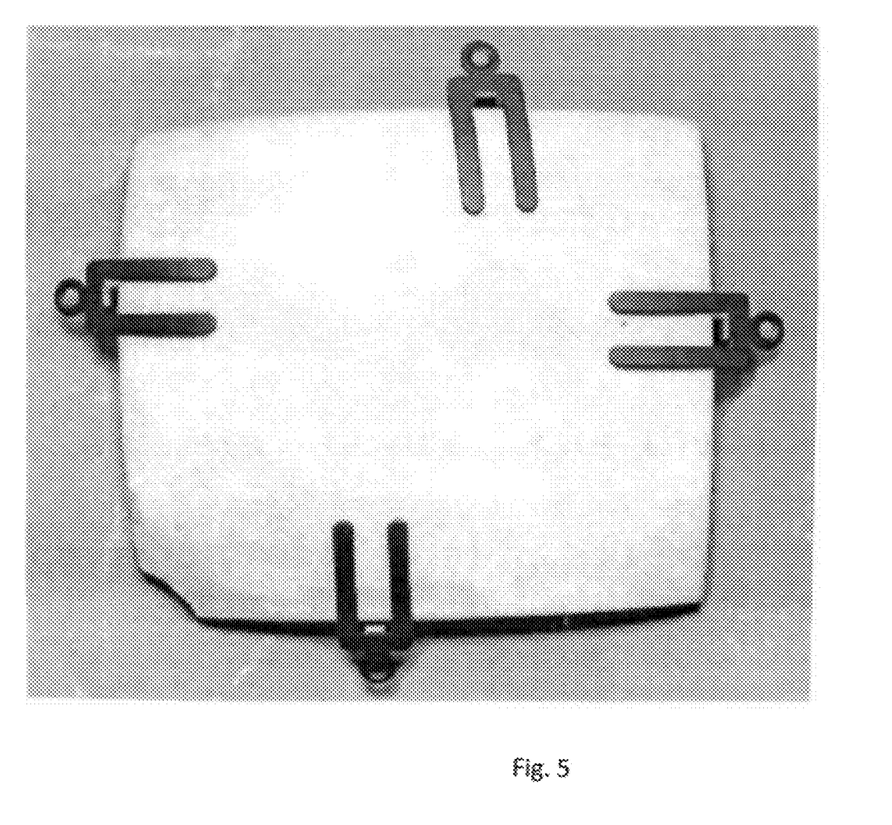
FIG. 5 shows: Top view of device applied on skull side edge.
Figure 6:
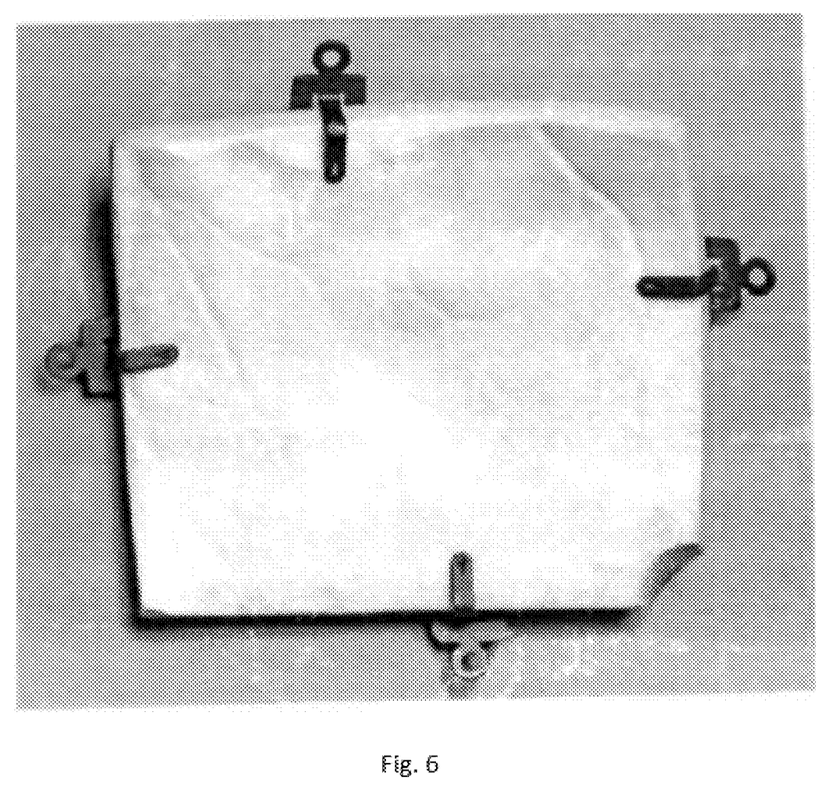
FIG. 6 shows: Bottom view of device applied on skull side edge.
Figure 7A:
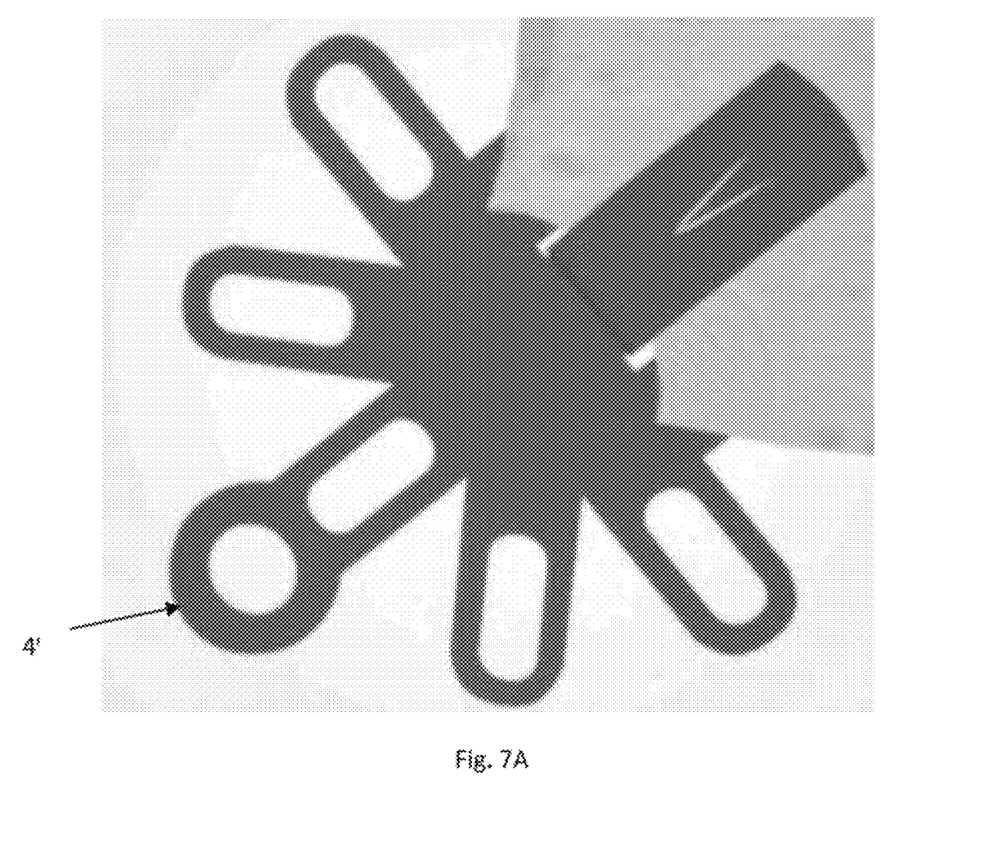
FIG. 7A shows: Bottom view of second embodiment of invention.
Figure 7B:
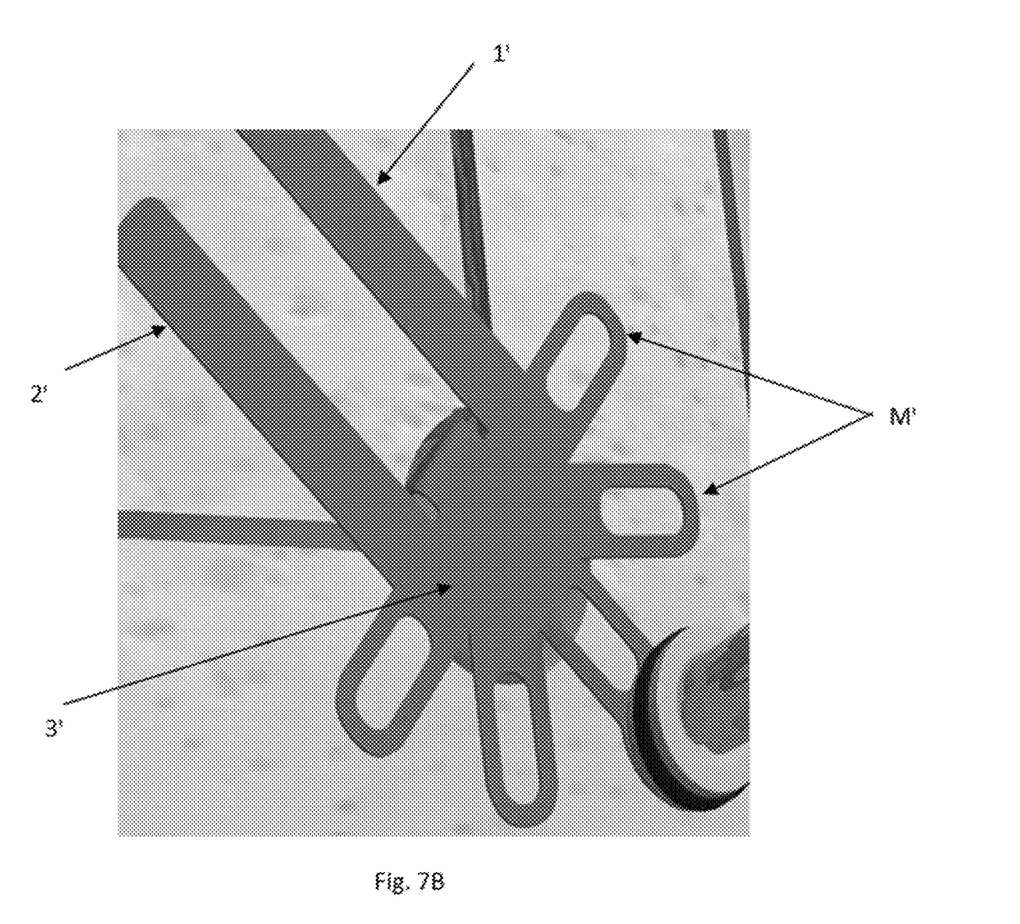
FIG. 7B shows: Top view of second embodiment of invention.

Implementation of Device During Neurosurgery of Head
  Creation of burr hole.
  Cutting the flap by means of a cutting tool starting from the hole and ending at the hole, wherein the flap has a rectilinear configuration.
  Measurement of thickness of four sides of the flap by means of a measuring gauge.
  Selection of size of device accordingly.
  Securing each side of flap with a respective device of invention, gap between two part (A, B) of which is equivalent to thickness of the flap of that particular side. The device is pushed on the flap as shown in the FIGS. 5 and 6.
  Securing corner of the flap adjoined to burr hole by means of a device as shown in FIGS. 7A and 7B. The device relies on the same inventive concept as already explained hereinabove with reference to FIG. 1-4. However, the connecting member (3') between two arms (1',2') of first part is integrated to multitude of projected members (M') directing outwards.
  Each of the projected members is flat and having a through hole at the centre. Here, the middle projected member is provided with an annular member (4') for passage of a screw so as to fasten the device to the skull. The middle projected member is selected to integrate annular member for maintaining symmetry.

These projected members are placed around the connecting member (3') so as to cover the burr hole. Rest of the construction of the device is similar to the first embodiment of invention.
  Positioning of the flap on the skull opening as in FIG. 8.
  Screwing each of the devices to the skull adjoined to the flap.

Advantageous Features

Very fast to operate.
Cost effective.
Does not need any special instrumentation for application.
Prevention of damage to brain.
Fast re-opening of craniotomy flap without need for special instrumentation.
Reusable.
Allows outward movement of cranial flap in case of brain edema.

It is to be noted that the present invention is susceptible to modifications, adaptations and changes by those skilled in the art.

Such variant embodiments employing the concepts and features of this invention are intended to be within the scope of the present invention, which is further set forth under the following claims:—

I claim:

1. A clip type cranial flap closing and anchoring device comprising:
  a single structure including:
    a first part having two arms, each arm comprising a top surface, a bottom surface, and a first length, wherein the two arms are parallel to each other along their length, and wherein the arms are directly joined at one end by a connecting member having a second length and wherein the bottom surfaces of the arms are configured to contact a top surface of a cranial flap, the arms and connecting member defining a U-shaped recess, the U-shaped recess extending from the connecting member and entirely between the parallel lengths of the two arms; and a second part having a L-shaped section and directly connected to the connecting member and configured to contact a bottom surface of said flap,
the device maintaining a gap between the first part and the second part to accommodate the flap, wherein the first part is fixedly secured to a third part for fastening the device to a skull,
wherein the top surfaces of the two arms of the first part are convex relative to the second part and are configured to remain intact with a top surface of a portion of a cranium,
wherein the L-shaped second part comprises an arm extending parallel to the U-shaped recess, between the two arms of the first part, and having a pin near an end thereof, wherein the pin projects at an angle upward and toward the second length,
wherein the two arms of the first part extend distally beyond the end of the arm of the L-shaped second part, and
wherein the arm of the L-shaped second part is entirely visible through the U-shaped recess.

2. The clip type cranial flap closing and anchoring device as claimed in claim 1, wherein said connecting member is fixedly secured to the third part, wherein the third part comprises an annular structure having a tapered hole at a center thereof so as to accommodate a screw.

3. The clip type cranial flap closing and anchoring device as claimed in claim 1, wherein the connecting member between the two arms of the first part comprises a plurality of projected members.

4. The clip type cranial flap closing and anchoring device as claimed in claim 3, wherein the projected members are flat and comprise a through hole, wherein one of said projected members is provided with an annular member for passage of a screw therethrough for fastening.

5. The clip type cranial flap closing and anchoring device as claimed in claim 1, wherein the gap between the first part and the second part is equivalent to thickness of the flap.

6. The clip type cranial flap closing and anchoring device as claimed in claim 4, wherein the device is configured such that the projected members cover a burr hole on the skull.

7. The clip type cranial flap closing and anchoring device as claimed in claim 1, wherein the device is a monolithic structure.

8. The clip type cranial flap closing and anchoring device as claimed in claim 1, wherein the first length is greater than the second length.

9. A clip type cranial flap closing and anchoring device comprising:
a single structure including:
a first part having two arms, each arm comprising a top surface, a bottom surface, and a first length, wherein the two arms are parallel to each other along their length, and wherein the arms are directly joined at one end by a connecting member having a second length and wherein the bottom surfaces of the arms are configured to contact a top surface of a cranial flap, the arms and connecting member defining a U-shaped, the U-shaped recess extending from the connecting member and entirely between the parallel lengths of the two arms; and a second part having a L-shaped section and directly connected to the connecting member and configured to contact a bottom surface of said flap; and
a plurality of projected members extending from the connecting member, at least one of the plurality of projecting members comprising an oblong opening therein,
wherein the top surfaces of the two arms of the first part are curved towards the L-shaped section, and
wherein the device maintains a gap between the first part and the second part to accommodate the flap, wherein the first part is fixedly secured to a third part for fastening the device to a skull,
wherein the L-shaped second part comprises an arm extending parallel to the U-shaped recess, between the two arms of the first part, and having a pin near an end thereof, wherein the pin projects at an angle upward and toward the second length,
wherein the two arms of the first part extend distally beyond the end of the arm of the L-shaped second part, and
wherein the arm of the L-shaped second part is entirely visible through the U-shaped recess.

10. The clip type cranial flap closing and anchoring device as claimed in claim 9, wherein the device is a monolithic structure.

11. The clip type cranial flap closing and anchoring device as claimed in claim 9, wherein the first length is greater than the second length.

* * * * *